United States Patent [19]

Siedle

[11] Patent Number: 4,549,018
[45] Date of Patent: Oct. 22, 1985

[54] RHODIUM- AND IRIDIUM-NITROGEN COMPLEX CATALYSTS

[75] Inventor: Allen R. Siedle, Lake Elmo, Minn.

[73] Assignee: Minnesota Mining and Manufacturing Company, St. Paul, Minn.

[21] Appl. No.: 522,472

[22] Filed: Aug. 11, 1983

Related U.S. Application Data

[62] Division of Ser. No. 246,104, Mar. 20, 1981, Pat. No. 4,414,376.

[51] Int. Cl.$^4$ .................. C07F 15/00; B01J 31/20; B01J 31/18; B01J 31/22
[52] U.S. Cl. .................. 544/225; 544/179; 544/180; 548/101; 548/108
[58] Field of Search .................. 544/225, 179, 180; 548/101, 108

[56] References Cited

U.S. PATENT DOCUMENTS

| 3,296,291 | 1/1967 | Chalk et al. ............... | 260/448.2 |
| 3,546,266 | 12/1970 | Coffey ............... | 260/448.2 |
| 3,960,810 | 6/1976 | Chandra et al. ............... | 260/46.5 |
| 4,262,107 | 4/1981 | Eckberg ............... | 528/15 |

FOREIGN PATENT DOCUMENTS 121509  5/1976  German Democratic Rep. .

OTHER PUBLICATIONS

Schretlick, Chem. Abs. 87, 39143v, (1976).
Balch et al., J. Organometallic Chem. 169, 97–105, (1979).
Banditelli, J. Organometallic Chem. 218, 229.
A. J. Chalk, J. Organometal. Chem.; 21, 207–213, (1970).
R. N. Haszeldine, R. V. Parish and D. J. Perry, J. Chem. Soc. (A) 683 (1969).

*Primary Examiner*—Mark L. Berch
*Attorney, Agent, or Firm*—Donald M. Sell; James A. Smith; Lorraine R. Sherman

[57] ABSTRACT

A process for addition curing organosilicone compositions using as catalysts rodium- or iridium-nitrogen complex compounds having the formulae:
(a) monometallic complexes, $(L)MX(Y)_2$, and
(b) bimetallic complexes, $(L)[RhX(CO)_2]_2$, wherein
  M is a rhodium or iridium metal atom,
  L is a single or fused heterocyclic ligand comprising at least one five- or six-membered ring, said ligand having 2 to 4 ring nitrogen atoms in the same ring,
  Y is an uncharged ligand that fills one or two coordination positions of the metal atom, and
  X is Cl, Br, I, or CN.

Preparation of the novel catalysts is disclosed. The cured compositions are useful as molded articles, such as gaskets, O-rings, and tubing.

16 Claims, No Drawings

RHODIUM-AND IRIDIUM-NITROGEN COMPLEX CATALYSTS

This is a division of application Ser. No. 246,104 filed Mar. 20, 1981, now U.S. Pat. No. 4,414,376.

TECHNICAL FIELD

This invention relates to rhodium- and iridium complex compounds and to their preparation. In another aspect, it relates to a process for hydrosilation using rhodium- or iridium complex compounds as catalysts. Compositions cured by hydrosilation are useful as molded articles.

BACKGROUND ART

In the presence of catalysts, curable organosilicone compositions undergo hydrosilation, a reaction involving the addition of a siliocon-hydrogen bond across a pair of aliphatic carbon atoms linked by multiple bonds. Catalysts used for reactions of this type are metals, most notably platinum, rhodium, iridium, and palladium, and compounds thereof. Hydrosilation has found widespread use in the production of silicone materials and organosilanes. Compared with platinum, relatively little work has been done on rhodium- and iridium-containing hydrosilation catalysts. Various chloro-rhodium compounds, wherein the valence of rhodium (Rh) is 1, particularly $[RhCl(CO)_2]_2$ and $RhCl(CO)[P(C_6H_5)_3]_3$ (A. J. Chalk, J. Organometal. Chem; 21, 207–213 (1970)), $[RhCl(C_2H_4)_2]_2$ (U.S. Pat. No. 3,296,291), and $RhCl[P(C_6H_5)_3]_3$ (U.S. Pat. No. 3,546,266), are disclosed in the literature to be hydrosilation catalysts. The mono- and bi-metallic pyrazine compounds, $(pyrazine)Rh(CO)_2Cl$ and $(pyrazine)Rh_2(CO)_4Cl_2$, have been disclosed (A. L. Balch et al., J. Organometal. Chem., 169, 97 (1979), but no use is specified. R. N. Haszeldine, R. V. Parish and D. J. Perry, J. Chem. Soc. (A), 683 (1969), found that $[(C_6H_5)_3P]_2Rh(CO)Cl$ was active as a hydrosilation catalyst but that the iridium analogue was inactive.

SUMMARY OF THE INVENTION

Briefly, in one aspect of the invention, there are provided novel rhodium- and iridium-nitrogen complexes useful as hydrosilation catalysts, the complexes being monometallic or bimetallic complex compounds. Another aspect of this invention provides a process for hydrosilation which comprises mixing an organosilicone composition with a catalytically effective amount of the rhodium- or iridium-nitrogen complex catalyst, optionally heating the resultant mixture, and recovering the resulting organosilanes or polysiloxanes.

A further aspect of this invention relates to a method of preparing rhodium- and iridium-nitrogen containing complexes useful as hydrosilation catalysts.

"Monometallic" refers to a complex having only one rhodium or iridium atom per molecule.

"Bimetallic" refers to a complex having two rhodium or iridium atoms per molecule.

"Addition curing" refers to a hydrosilation reaction in which compounds having more than one pair of aliphatic carbon atoms linked by multiple bonds and compounds having more than one silicon-hydrogen bond react together to form a crosslinked polymer.

"Pot life" is the time during which the composition containing the curable organosilicone components and the catalyst remains sufficiently to be easily coatable, extrudable, or otherwise processed.

The use of the complexes of this invention as catalysts overcomes problems often associated with platinum-containing hydrosilation catalysts known in the art, such as instability, inefficiency, poor dispersibility in polymerization media, difficult synthesis procedures, and susceptibility of catalyst poisoning. In contrast, the complexes of this invention have increased stability, increased dispersibility in reaction media, give lower activation temperatures, are more active catalysts, provide curable organosilicone compositions having longer pot life, and are less susceptible to catalytic poisoning. Lower activation temperature is particularly advantageous when it is desired to carry out the curing process on a thermally labile substrate. It is a useful processing feature to have long ambient gel times (i.e., greater than 1 hour) so that the curable, catalyst-containing organosilicone composition can be maintained in a fluid state prior to conversion into a finished article.

DETAILED DESCRIPTION

The complexes used in the hydrosilation process of the present invention are the classes of compounds having the following formulae:

(a) monometallic complexes, $(L)MX(Y)_2$, and
(b) bimetallic complexes, $(L)[RhX(CO)_2]_2$ wherein M is a rhodium of iridium metal atom, L is a single or fused heterocyclic ligand comprising at least one five- or six-member ring, said ligand having 2 to 4 ring nitrogen atoms in the same ring, Y is an uncharged ligand that fills one or two coordination positions of the metal atom, such a mono- or di-olefin or an alkyl or aryl substituted mono- or di-olefin, said olefin having up to 25 carbon atoms or CO, and X is Cl, Br, I, or CN.

Y, an uncharged ligand, coordinates to the central metal atom in the complex and occupies one coordination position when Y is CO or a mono-olefin, such as ethylene, propylene, butylene, or styrene, or substituted derivatives thereof, or it may occupy two coordination positions when Y is a di-olefin such as 1,5-cyclooctadiene (COD), 1,4-cyclohexadiene (CHD), or bicyclo[2.2.1]heptadiene, or substituted derivatives of the di-olefins.

All of the hydrosilation catalysts of the present invention are novel complex compounds except the mono and bimetallic compounds mentioned above where L is pyrazine, which compounds (where the two N atoms in the six-membered ring are in the 1,4 position) have been disclosed previously.

The single and fused ring heterocyclic ligand, L, which preferably is a cyclic structure containing two nitrogen atoms, single or poylnuclear fused ring dinitrogen-containing which structure can have one, or two or three polynuclear fused rings. The nitrogen atoms in the same ring may be in any positions; they need not be para to each other. The double-fused ring cyclic structure may be

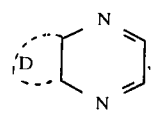

wherein the encircled letter D denotes a 6-member carbocyclic aromatic or heterocyclic aromatic ring fused with the depicted di-nitrogen heterocycle. Quinoxaline is the prefererd species. In the triple-fused ring systems,

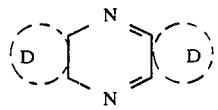

the encircled letters D each denote a 6-member carbocyclic aromatic or heterocyclic aromatic ring fused with the depicted di-nitrogen heterocycle. Phenazine in this instance is the preferred species; phenazine oxide is also useful. Other useful ligands, of the single ring type, in addition to pyrazine, are the five-membered ring structures imidazole, and 1,2,4-triazole. The polynitrogen-containing single or polynuclear fused ring structure is important in providing increased stability and longer pot life to these novel catalysts when compared to prior art hydrosilation catalysts.

General preparative methods for the complexes described above will now be discussed.

Monometallic catalysts of the type $(L)MX(Y)_2$, wherein L, Y, and X are as defined above, are prepared by combining L, the polynitrogen ligand, and the dimer of the type $[MY_2X]_2$ in a 2:1 mole ratio in an organic solvent, such as benzene, toluene, methanol, acetonitrile, methylene chloride, or chloroform. The preferred solvent is methylene chloride. The complex salts are recovered from the reaction mixture. Starting materials $[M(olefin)_2X]_2$, wherein M and X are as defined above, and $[Rh(CO)_2Cl]_2$ are commercially available. Useful polynitrogen-containing single or fused ring substances, L, are available from Aldrich Chemical Co. Preferably the olefin has the structure $R_2C = CR_2$, each R is independently H, an alkyl group of up to 20 carbon atoms, or an aryl group having up to 10, and preferably 6 ring carbon atoms, with the proviso that not more than one R group on each carbon atom is aryl. The preferred olefinic ligand is COD.

Because L contains more than 1 donor nitrogen atom, additional novel catalytically active bimetallic compounds of the formula $L[RhX(CO)_2]_2$ can be prepared, in which at least two ring nitrogen atoms in the heterocyclic ligand are linked to rhodium atoms. These compounds of the formula $L[RhX(CO)_2]_2$ are formed by combining L and $[Rh(CO)_2X]_2$ in a 1:1 molar ratio, wherein L and X are as defined above. They are removed from the reaction mixture and are easily isolated by filtration.

The amount of complex of the present invention to be used in the curable organosilicone compositions varies within a wide range, i.e., 1 to 1000 ppm of rhodium or iridium metal in the curable composition.

Addition cure or hydrosilation reactions produce organosilanes and polysiloxanes. The organosilicone compositions are formable materials ranging from thin pastes to stiff plastic, dough-like substances. They may be shaped, as by molding or extruding, after which the article is converted to a rubbery state by heating to effect cure. The silicone rubber fabricated articles may be, for example, O-rings, gaskets, or tubing.

Objects and advantages of this invention are further illustrated by the following examples, but the particular materials and amounts thereof recited in these examples, as well as other conditions and details, should not be construed to unduly limit this invention.

EXAMPLE 1

(Phenazine)RhCl($C_8H_{12}$)

To 1.25 g (2.5 mmole) [RhCl(COD)]$_2$ in 30 ml. acetonitrile was added 0.90 g (5.0 mmole) phenazine in a minimum amount of warm acetonitrile. Needle crystals began to separate from the orange solution and, after 0.5 hr., they were collected on a filter, washed with fresh solvent and vacuum dried. The yield was 1.6 g (75%). Spectroscopic and elemental analyses confirmed the crystalline material to be (phenazine)RhCl($C_8H_{12}$).

Using the method just described, (phenazine)RhBr($C_8H_{12}$) and (phenazine-N-oxide)RhCl($C_8H_{12}$) were prepared using [RhBr(COD)]$_2$ or phenazine-N-oxide as starting materials. Spectroscopic and elemental analyses confirmed the identity of these compounds.

EXAMPLE 2

(Quinoxaline)RhCl($C_8H_{12}$)

Quinoxaline, 1.66 mmole in 2 ml. acetonitrile, was added to a solution of 0.41 g. (0.83 mmole) [RhCl(COD)]$_2$ in 20 ml. of the same solvent. The mixture was evaporated to 2 ml. with a nitrogen jet. The remaining solution was heated to boiling and filtered. On cooling, the product separated as yellow nodules. It was filtered and vacuum dried; yield 0.2 g. (32%). Spectroscopic and elemental analyses confirmed and identity of the product to be (Quinoxaline)RhCl($C_8H_{12}$).

EXAMPLE 3

(Phenazine)IrCl($C_8H_{12}$)

Cyclooctadiene iridium(I) chloride dimer was prepared from hydrated $IrCl_3$ by the method disclosed in "Organometallic Synthesis", 1, R. Bruce King, Academic Press, N.Y., 1965, p. 132. A 0.95 g. sample of this crude dimer was dissolved in 25 ml. methylene chloride and the solution filtered. Phenazine, 0.51 g. (2.8 mmole) was added. The resulting orange solution was evaporated to a small volume under reduced pressure and diluted with ethanol. On cooling to $-20°$ C., 0.8 g. of red-brown solid separated. This was recrystallized from hot acetonitrile to give 0.20 g. of the iridium complex as dark brown needles. Spectroscopic and elemental analyses confirmed the identity of the product to be (phenazine)IrCl($C_8H_{12}$).

EXAMPLE 4

(Phenazine)RhCl(CO)$_2$

A solution of 0.36 g. (12 mmole) phenazine in 10 ml. benzene was added dropwise to 0.4 g. (1 mmole) resublimed [RhCl(CO)$_2$]$_2$ in 35 ml. benzene. The resulting orange solution was evaporated to 3 ml. under reduced pressure and diluted with hexane to give 0.60 g. (80%) of product as yellow needles. Spectroscopic and elemental analyses confirmed the identity of the product to be (phenazine)RhCl(CO)$_2$. The infrared spectrum contained two Rh-carbonyl stretching bands indicative of cis stereochemistry.

Using the method of this EXAMPLE, (phenazine-N-oxide)RhCl(CO)$_2$ was prepared utilizing phenazine-N-oxide in place of phenazine and its identity was confirmed by spectroscopic and elemental analyses.

EXAMPLE 5

(Phenazine)[RhCl(CO)$_2$]$_2$

This bimetallic compound was prepared using the method of EXAMPLE 4 and half the amount of phenazine. The yield of orange, crystalline material was 0.45 g. (79%). Spectroscopic and elemental analyses confirmed the identity of the product to be (phenazine)[RhCl(CO)$_2$]$_2$.

EXAMPLE 6

(Imidazole)RhCl(CO)$_2$

A solution of 0.19 g (0.5 mmole) [Rh(CO)$_2$Cl]$_2$ in 10 ml chloroform was added to 0.069 g (1 mmole) imidazole in 3 ml of the same solvent. The yellow solution was diluted to the cloud point with heptane and then concentrated without heating on the rotary evaporator. Yellow crystals of (imidazole)RhCl(CO)$_2$ separated and were collected on a filter and vacuum dried. The yield was 0.20 g, m.p. 77°–80° C. Elemental analyses confirmed the identity of the product to be (imidazole)RhCl(CO)$_2$. The infrared spectrum contained two Rh-carbonyl stretching bands indicative of cis stereochemistry.

Orange crystals of (1,2,4-triazole)RhCl(CO)$_2$ (m.p. decomposes) were prepared by a similar method using 1,3,4-triazine in place of imidazole. Spectroscopic and elemental analyses identified this product.

EXAMPLE 7

(Phenazine)IrCl(CO)$_2$

A mixture of 0.31 g (1 mmole) of polymeric [IrCl(CO)$_3$], and 0.18 g (1 mmole) of phenazine in 25 ml acetonitrile was stirred under reflux for 16 hr, then filtered. The filtrate was diluted to the cloud point with hexane and then cooled to $-20°$. The yellow crystals which separated were collected on a filter. Unreacted phenazine was removed from this crude product by heating the material in a sublimer (80° C., $3 \times 10^{-3}$ mm.) fitted with a dry ice cooled probe. The yield of pure, yellow crystalline product was 0.075 g, m.p. 195° C. Spectroscopic and elemental analyses indicated the product to be (phenazine)IrCl(CO)$_2$. the infrared spectrum contained two Ir-carbonyl stretching bands indicative of cis stereochemistry.

EXAMPLE 8

Use of Complexes as Catalysts in Hydrosilation Reactions

Utility of several rhodium complexes as hydrosilation catalysts was evaluated using two vinyl functional siloxane polymers, A and B, described below in TABLES I and II. A solution was prepared by adding the rhodium compound in 2 ml. dichloromethane to the vinyl functional siloxane and evaporating the dichlormethane. Typical rhodium concentrations were 25–50 ppm metal by weight. DC-1107, (polyhydrosiloxane crosslinker, (CH$_3$)$_3$Si[CH$_3$Si(H)O]$_{35}$Si(Ch$_3$)$_3$, Dow Corning Co.), 0.5 ml., was added to 10 ml. of the catalyst-containing vinylsiloxane, and the gel times (i.e., the time it takes for crosslinking to a rubbery state to occur as determined by ASTM method D-2471-71, reapproved 1979) were measured. The more efficient the catalyst, the more rapid is the crosslinking hydrosilation reaction and, therefore, the shorter is the gel time. For comparison, certain runs were made with controls using compounds known in the prior art i.e., [(COD)RhCl]$_2$ and (pyridine)RhCl(COD).

TABLE I $$CH_2=CH-\underset{\underset{CH_3}{|}}{\overset{\overset{CH_3}{|}}{Si}}-O+(CH_3)_2SiO+_{122}(Si-O+_3\underset{\underset{CH_3}{|}}{\overset{\overset{CH_3}{|}}{Si}}-CH=CH_2 \quad A$$
$$\underset{\underset{CH_2}{\|}}{CH}$$

| Run | Catalyst (used with polymer A and DC-1107) | Rh, ppm | Gel time, room temp., min. | Gel time, 90° C., sec. | Temp. for gel time $\leq 5$ sec, °C. |
|---|---|---|---|---|---|
| 1. | (phenazine)RhBr(COD) | 25 | >250 | 30 | 120 |
| 2. | (phanazine)RhCl(CO)$_2$ | 25 | 120 | 13 | 105 |
| 3. | [(COD)RhCl]$_2$* | 50 | 51 | 17 | 110 |
| 4. | (pyridine)RhCl(COD)* | 25 | 130 | 23 | 115 |

*control

Run 2 had a room temperature gel time comparable to other compositions tested, but its gel time at 90° C. was very rapid, indicating it was an effective catalyst at elevated temperatures.

TABLE II $$CH_2=CH-\underset{\underset{CH_3}{|}}{\overset{\overset{CH_3}{|}}{Si}}-O+(CH_3)_2SiO+_{133}Si-CH=CH_2 \quad B$$

| Run | Catalyst (used with polymer B and DC-1107) | Rh, ppm | Gel time, room temp., min. | Gel time, 90° C., sec. | Temp. for gel time $\leq 5$ sec, °C. |
|---|---|---|---|---|---|
| 5. | (phenazine)RhCl(COD) | 25 | 83 | 12 | 105 |
| 6. | (pyridine)RhCl(COD)* | 25 | 80 | 13 | 115 |
| 7. | (phenazine)RhCl(CO)$_2$ | 25 | 160 | 10 | 105 |
| 8. | [(COD)RhCl]$_2$* | 50 | 30 | 10 | 100 |

*control

Run 1 had an unusually long gel time at room temperature, this indicating that (phenazine)RhBr(COD) was useful for operations requiring a long pot life. (Phenazine)RhBr(COD) was an effective catalyst at 120° C. Run 7 was very stable at room temperature yet could be activated at a relatively low temperature of 105° C.

The composition of Run 7 was poured into a heated (110° C.) mold which was shaped as a gasket. A solid rubbery gasket was extracted from the mold after 15 min indicating that the hydrosilation reaction produced a useful product.

EXAMPLE 9

Use of (pyrazine)[RhCl(CO)$_2$]$_2$ as catalyst in Hydrosilation Reactions

A mixture was prepared by adding the rhodium complex compound (pyrazine)[RhCl(CO)$_2$]$_2$, prepared by the method disclosed in the reference to this complex under the section entitled Background Art above, and 2 ml. dichloromethane to the vinyl functional siloxane represented by polymer A in EXAMPLE 8 and evaporating the dichloromethane. The rhodium concentration was 50 ppm metal by weight. DC-1107, (polyhydrosiloxane crosslinker, (CH$_3$)$_3$Si[CH$_3$Si(H)O]$_{35}$Si(CH$_3$)$_3$, Dow Corning Co.), 0.5 ml., was added to 10 ml. of the catalyst-containing vinyl-siloxane. The composition was poured into a heated (110° C.) mold which was shaped as a gasket. A solid rubbery gasket was extracted from the mold after 15 min indicating that the hydrosilation reaction produced a useful product.

Various modifications and alterations of this invention will become apparent to those skilled in the art without departing from the scope and spirit of this invention, and it should be understood that this invention is not to be unduly limited to the illustrative embodiments set forth herein.

I claim:

1. Rhodium- and iridium-nitrogen complex compound selected from classes of compounds having the general formulae:
   (a) monometallic complexes, (L)MX(Y)$_2$, and
   (b) bimetallic complexes, (phenazine)[RhX(CO)$_2$], wherein
   M is a rhodium or iridium metal atom,
   L is a single ring or fused 2-, or 3-ring heterocyclic ligand comprising at least one 6-member ring which can be fused to one or two other 6-member carbocyclic aromatic rings, said ligand having only 2 nitrogen ring atoms in the same ring, at least one of which nitrogen atoms is bonded to a rhodium or iridium atom, with the proviso that the nitrogen atoms are in the 1,4-position,
   Y is uncharged monodentate ligand that fills only one coordination position of the metal atom and is selected from CO and mono-olefins which are unsubstituted or substituted by alkyl or phenyl, said mono-olefin being unsubstituted or substituted by alkyl or phenyl having up to 25 carbon atoms, and
   X is Cl, Br, I, or Cn.

2. Rhodium- and iridium-nitrogen complex compounds selected from the classes of compounds having the general formulae:
   (a) monometallic complexes, (L)MX(Y)$_2$, and
   (b) bimetallic complexes, (phenazine)[RhX(CO)$_2$]$_2$, wherein
   M is a rhodium or iridium metal atom,
   L is phenazine, phenazine oxide, or quinoxaline,
   Y is CO, ethylene, propylene, butylene, or styrene, and
   X is Cl, Br, I, or CN.

3. Rhodium- and iridium-nitrogen complex compounds selected from class of compounds having the formula:
   monometallic complexes, (L)MX(uncharged ligand) wherein
   M is a rhodium or iridium metal atom,
   L is a single ring or fused 2-, or 3- ring heterocyclic ligand comprising at least one 6-member ring which can be fused to one or two other 6-member carbocyclic aromatic rings, said ligand having only 2 nitrogen ring atoms in the same ring, at least one of which nitrogen atoms is bonded to a rhodium or iridium atom, with the proviso that the nitrogen atoms are in the 1,4-position,
   uncharged ligand coordinates to the central metal atom in the complex and is a di-olefin which occupies two coordination positions, said di-olefin being unsubstituted or substituted by alkyl or phenyl and having up to 25 carbon atoms, and
   X is Cl, Br, I or CN.

4. The complex compound (phenazine-N-oxide)RhCl(CO)$_2$.

5. The complex compound according to claim 3 wherein uncharged ligand is 1,5-cyclooctadiene, bicyclo[2.2.1]heptadiene, and 1,4-cyclohexadiene.

6. The complex compound (phenazine-N-oxide)RhCl(C$_8$H$_{12}$) according to claim 3.

7. The complex compound according to claim 1 wherein L is phenazine, phenazine oxide, or quinoxaline.

8. The complex compound according to claim 1 wherein L represents a quinoxaline compound.

9. The complex compound according to claim 1 wherein L represents a phenazine compound.

10. The complex compound (phenazine)RhCl(CO)$_2$ according to claim 2.

11. The complex compound (phenazine)RhCl(C$_8$H$_{12}$) according to claim 3.

12. The complex compound (phenazine)[RhCl(CO)$_2$]$_2$ according to claim 2.

13. The complex compound according to claim 1 wherein L represents a pyrazine compound.

14. The complex compound (quinoxaline)RhCl(C$_8$H$_{12}$) according to claim 3.

15. The complex compound (phenazine)IrCl(C$_8$H$_{12}$) according to claim 3.

16. The complex compound (phenazine)IrCl(CO)$_2$ according to claim 2.

* * * * *